United States Patent
Eto

(10) Patent No.: US 12,072,325 B2
(45) Date of Patent: Aug. 27, 2024

(54) INFORMATION PROCESSING APPARATUS, INFORMATION PROCESSING METHOD, AND PROGRAM

(71) Applicant: NEC Corporation, Tokyo (JP)

(72) Inventor: Riki Eto, Tokyo (JP)

(73) Assignee: NEC CORPORATION, Tokyo (JP)

( * ) Notice: Subject to any disclaimer, the term of this patent is extended or adjusted under 35 U.S.C. 154(b) by 680 days.

(21) Appl. No.: 17/279,285

(22) PCT Filed: Sep. 27, 2018

(86) PCT No.: PCT/JP2018/036136
§ 371 (c)(1),
(2) Date: Mar. 24, 2021

(87) PCT Pub. No.: WO2020/065890
PCT Pub. Date: Apr. 2, 2020

(65) Prior Publication Data
US 2021/0405004 A1 Dec. 30, 2021

(51) Int. Cl.
*G01N 33/00* (2006.01)
*G06N 5/04* (2023.01)

(52) U.S. Cl.
CPC ........... *G01N 33/0001* (2013.01); *G06N 5/04* (2013.01)

(58) Field of Classification Search
None
See application file for complete search history.

(56) References Cited

U.S. PATENT DOCUMENTS

| 2006/0191319 | A1* | 8/2006 | Kurup | G01N 33/0034 73/23.34 |
|---|---|---|---|---|
| 2016/0261115 | A1* | 9/2016 | Asati | H02J 3/14 |
| 2018/0189242 | A1 | 7/2018 | Fukushima et al. | |
| 2018/0340921 | A1* | 11/2018 | Shim | G01N 30/62 |
| 2019/0317066 | A1 | 10/2019 | Imamura et al. | |

(Continued)

FOREIGN PATENT DOCUMENTS

| JP | 2016-146039 A | 8/2016 |
|---|---|---|
| JP | 2018-087722 A | 6/2018 |

(Continued)

OTHER PUBLICATIONS

International Search Report for PCT Application No. PCT/JP2018/036136, mailed on Dec. 18, 2018.

(Continued)

*Primary Examiner* — Roy Y Yi

(57) ABSTRACT

An information processing apparatus (20) includes a use environment information acquisition unit (210), a model selection unit (220), and a prediction unit (230). The use environment information acquisition unit (210) acquires use environment information indicating a use environment of a physical system having input-output. The model selection unit (220) selects, from a storage unit storing a plurality of prediction models of the physical system in association with section information indicating a section based on the use environment, a prediction model being associated with section information of a section matching the use environment indicated by the use environment information. The prediction unit (230) performs prediction based on output of the physical system by use of the selected prediction model.

5 Claims, 7 Drawing Sheets

(56) References Cited

U.S. PATENT DOCUMENTS

2019/0325671 A1* 10/2019 Takasu ............... F02D 41/1405
2020/0027013 A1    1/2020 Eto et al.

FOREIGN PATENT DOCUMENTS

| JP | 2018-092511 A | 6/2018 |
| JP | 2018-109876 A | 7/2018 |
| JP | 2018-112444 A | 7/2018 |
| JP | 2018-132325 A | 8/2018 |
| WO | 2018/097047 A1 | 5/2018 |
| WO | 2018/150798 A1 | 8/2018 |

OTHER PUBLICATIONS

Riki Eto et al., "Fully-Automatic Bayesian Piecewise Sparse Linear Models", Proceedings of the Seventeenth International Conference on Artificial Intelligence and Statistics, 2014, PMLR 33, pp. 238-246.

Japanese Office Action for JP Application No. 2020-547772 mailed on Mar. 22, 2022 with English Translation.

1 JP Office Action for JP Application No. 2020-547772, mailed on Aug. 16, 2022 with English Translation.

* cited by examiner

FIG. 7

| SECTION INFORMATION | PREDICTION MODEL INFORMATION |
|---|---|
| TEMPERATURE T > THRESHOLD VALUE $T_1$ AND TEMPERATURE T < THRESHOLD VALUE $T_2$ | PREDICTION MODEL 1 |
| TEMPERATURE T > THRESHOLD VALUE $T_1$ AND TEMPERATURE T ≧ THRESHOLD VALUE $T_2$ | PREDICTION MODEL 2 |
| TEMPERATURE T ≦ THRESHOLD VALUE $T_1$ AND HUMIDITY H > THRESHOLD VALUE $H_1$ | PREDICTION MODEL 3 |
| TEMPERATURE T ≦ THRESHOLD VALUE $T_1$ AND HUMIDITY H ≦ THRESHOLD VALUE $H_1$ | PREDICTION MODEL 4 |

…

INFORMATION PROCESSING APPARATUS, INFORMATION PROCESSING METHOD, AND PROGRAM

This application is a National Stage Entry of PCT/JP2018/036136 filed on Sep. 27, 2018, the contents of all of which are incorporated herein by reference, in their entirety.

TECHNICAL FIELD

The present invention relates to an information processing apparatus, a transfer function generation method, and a program.

BACKGROUND ART

There has been developed a technique for utilizing a physical system that performs a response (output) for some input, and thus obtaining another piece of information from output of the physical system.

For example, a technique for acquiring, by measuring a gas with a sensor, information relating to the gas has been developed. For example, PTL 1 described below discloses a technique for identifying an unknown sample by using a transfer function determined based on output of a chemical sensor for input of the unknown sample. Specifically, a technique for 1) providing input in which an amount of an unknown sample changes over time to a chemical sensor, 2) measuring a response changing over time from the chemical sensor, 3) determining, based on the input and the response, a transfer function of the unknown sample, and 4) identifying, based on the determined transfer function, the unknown sample has been disclosed.

CITATION LIST

Patent Literature

[PTL 1] Japanese Patent Application Publication No. 2018-087722

Non Patent Literature

[NPL 1] Riki Eto, Ryohei Fujimaki, Satoshi Morinaga, Hiroshi Tamano, "Fully-Automatic Bayesian Piecewise Sparse Linear Models", Proceedings of the Seventeenth International Conference on Artificial Intelligence and Statistics, PMLR 33:238-246, 2014.

SUMMARY OF INVENTION

Technical Problem

However, the technique of PTL 1 described above is premised on a linearity of an input-output relation of a physical system such as a sensor. Thus, when the input-output relation of the physical system is non-linear, there is a concern that accuracy of identification (prediction) deteriorates.

The present invention has been made in view of the problem described above. One of objects of the present invention is to provide a technique for performing, with satisfactory accuracy, prediction using output of a physical system in which an input-output relation is non-linear.

Solution to Problem

An information processing apparatus according to the present invention includes:

a use environment information acquisition unit that acquires use environment information indicating a use environment of a physical system having input-output;

a model selection unit that selects, from a storage unit storing a plurality of prediction models of the physical system in association with section information indicating a section based on the use environment, a prediction model being associated with section information of a section matching the use environment indicated by the use environment information; and a prediction unit that performs prediction based on output of the physical system by use of the selected prediction model.

An information processing method executed by a computer according to the present invention includes:

acquiring use environment information indicating a use environment of a physical system having input-output;

selecting, from a storage unit storing a plurality of prediction models of the physical system in association with section information indicating a section based on the use environment, a prediction model being associated with section information of a section matching the use environment indicated by the use environment information; and performing prediction based on output of the physical system by use of the selected prediction model.

A program according to the present invention causes a computer to execute the information processing method described above.

Advantageous Effects of Invention

The present invention enables a characteristic of a physical system to be expressed by a transfer function, including a case where a characteristic of the physical system is non-linear.

BRIEF DESCRIPTION OF DRAWINGS

The above-described object, other objects, features, and advantages effects will become more apparent from a preferred example embodiment described below and the following accompanying drawings.

FIG. 7 is a diagram illustrating one example of association information between the prediction model and section information.

EXAMPLE EMBODIMENT

Hereinafter, an example embodiment according to the present invention is described by use of drawings. Note that, in all of the drawings, a similar component is assigned with a similar reference sign, and description thereof is omitted, as appropriate.

Note that, in the following description, each component of each apparatus does not indicate a configuration of a hardware unit but indicates a block of a function unit, unless otherwise specially described. Each component of each apparatus is achieved by any combination of hardware and software mainly including a CPU of any computer, a memory, a program that achieves a component of the present figure loaded onto the memory, a storage medium such as a hard disk that stores the program, and an interface for network connection. As an achieving method therefor and an apparatus, there are various modified examples.

Example Embodiment

Overview

Figure 1:
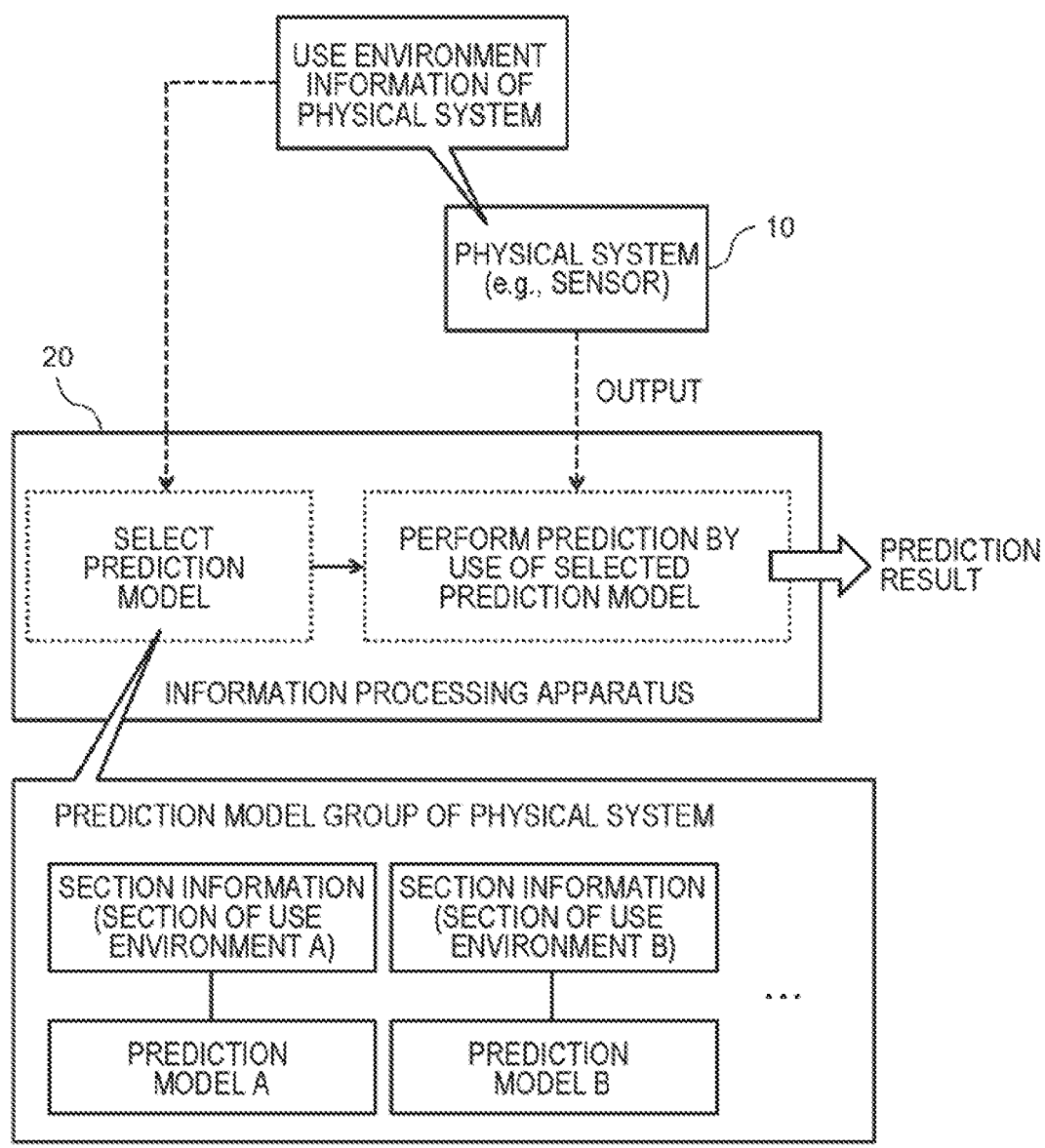
FIG. 1 is a diagram for describing an overview of an information processing apparatus according to the present invention.

First, an overview of an information processing apparatus 20 according to the present invention is described by use of FIG. 1. FIG. 1 is a diagram for describing an overview of the information processing apparatus 20 according to the present invention. The information processing apparatus 20 according to the present invention selects, according to a use environment of a physical system 10 (e.g., a sensor), a model (hereinafter, also referred to as a "prediction model") for performing prediction, based on output of the physical system 10 that performs some output for given input, and performs prediction by use of the selected prediction model.

Herein, with regard to the physical system 10 to be a target in the present invention, a plurality of prediction models are generated in advance. For example, as illustrated, a plurality of prediction models of the physical system 10 are stored in a predetermined storage area accessible by the information processing apparatus 20, in association with section information indicating a section matching a use environment of the physical system 10. The information processing apparatus 20 selects, based on information (hereinafter, also referred to as "use environment information") indicating a use environment of the physical system 10 to be a target, a prediction model related to the use environment. The information processing apparatus 20 performs prediction by use of the selected prediction model, based on output of the physical system 10, and outputs a result of the prediction.

Functional Configuration Example

Figure 2:
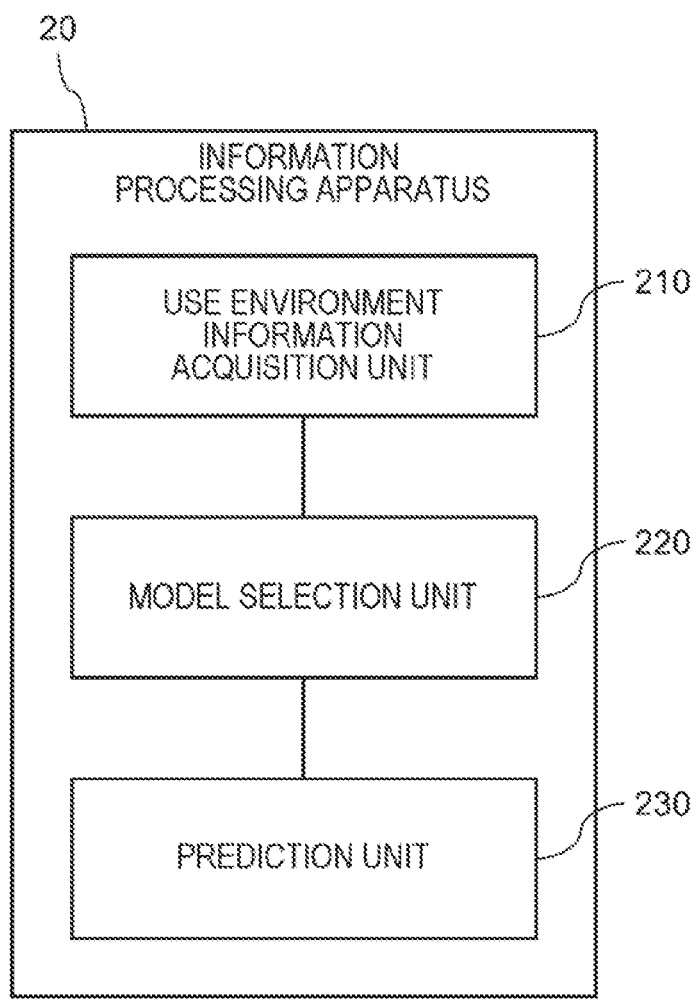
FIG. 2 is a diagram illustrating a functional configuration example of the information processing apparatus.

FIG. 2 is a diagram illustrating a functional configuration example of the information processing apparatus 20. As illustrated in FIG. 2, the information processing apparatus 20 includes a use environment information acquisition unit 210, a model selection unit 220, and a prediction unit 230.

The use environment information acquisition unit 210 acquires use environment information of a physical system having input-output.

The use environment information acquisition unit 210 acquires use environment information indicating a use environment of the physical system 10. The model selection unit 220 selects one prediction model from among a plurality of prediction models by use of the use environment information acquired by the use environment information acquisition unit 210. Herein, as described by use of FIG. 1, a plurality of prediction models are stored in a predetermined storage area in association with section information indicating a section based on a use environment. The model selection unit 220 selects a prediction model being associated with section information of a section matching the use environment indicated by the use environment information acquired by the use environment information acquisition unit 210. The prediction unit 230 performs prediction based on output of the physical system 10 by use of the prediction model selected by the model selection unit 220, and outputs a result of the prediction to a non-illustrated output apparatus (e.g., a display or the like).

Regarding Physical System

A sensor can be cited as one example of a physical system having input-output. A sensor is an apparatus that obtains, as input, a state or a property of an object to be a detection target, or information such as a physical amount, converts the input into an electric signal, and outputs the electric signal. Note that, a type of a sensor is not specifically limited. For example, while an example of an odor sensor is described below, a sensor may be a sensor that senses a mechanical amount, light, heat, a radiation, electricity, magnetism, or the like.

Figure 3:
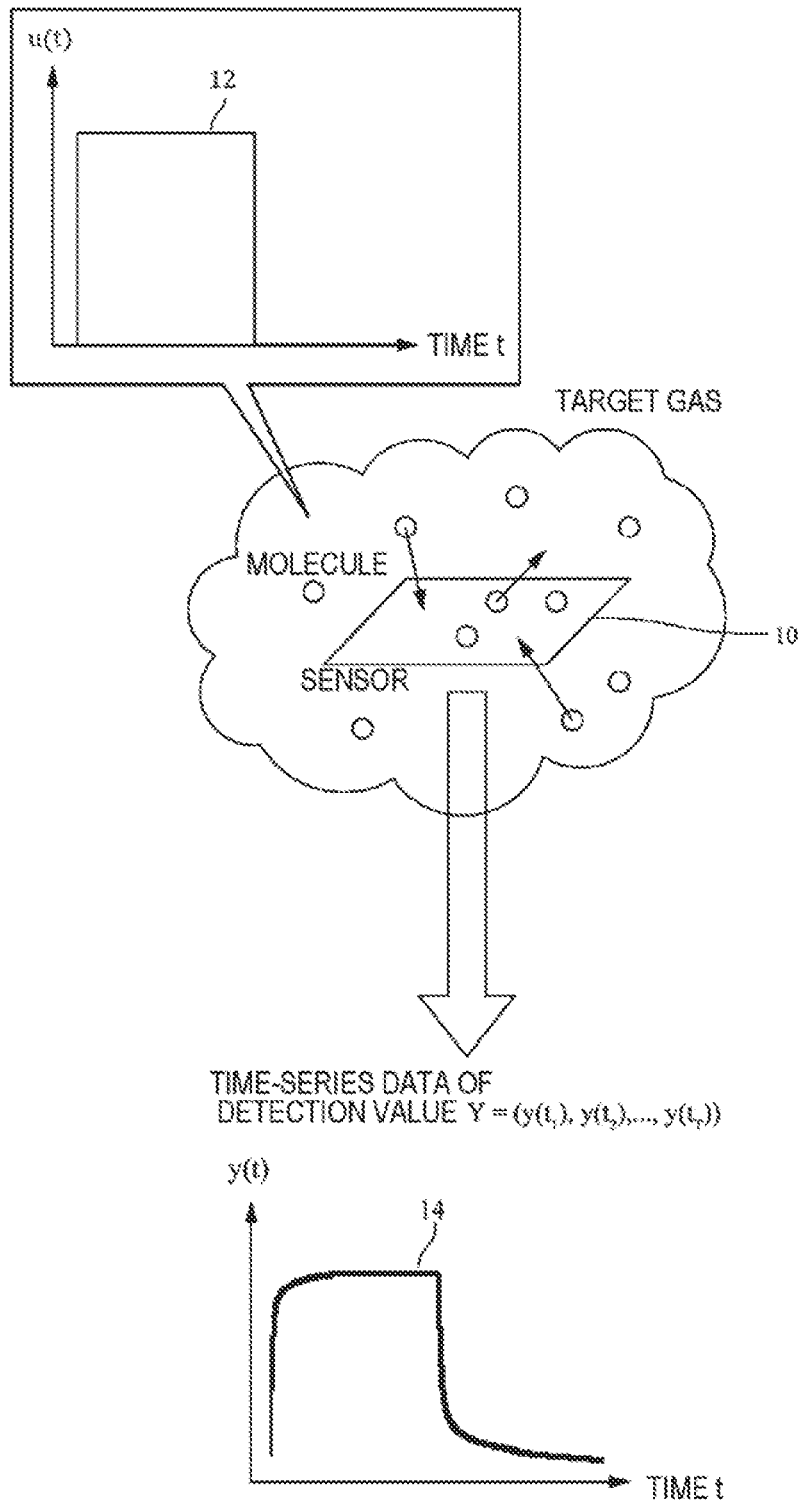
FIG. 3 is a diagram for describing input-output time-series data of a sensor cited as one example of a physical system.

FIG. 3 is a diagram for describing input-output time-series data of a sensor cited as one example of a physical system. In FIG. 3, the sensor (physical system 10) is a sensor (an odor sensor that senses an odor component) having a receptor to which a molecule (odor component) contained in a gas adheres, and changing in detection value in response to adhesion and separation of the molecule in the receptor. Note that, a gas sensed by the sensor is referred to as a target gas. Herein, input to a sensor exists in a period of time in which the sensor senses a target gas. From a different perspective, a period (sampling period) of a signal that controls sampling and a purge of a target gas is input to a sensor. Note that, the "sampling" unit exposing a sensor to a target gas, and the "purge" unit eliminating the target gas from the sensor. Time-series data in the sampling period (signal input value) are referred to as input time-series data 12. Time-series data of a detection value output from a sensor according to input indicated by the input time-series data 12 are referred to as output time-series data 14. In the following description, when needed, the input time-series data 12 and the output time-series data 14 are also referred to as U and Y, respectively. A signal input value of the input time-series data 12 at a time t and a detection value of the output time-series data 14 at the time t are also referred to as u(t) and y(t), respectively. U denotes a vector in which u(t) is enumerated. Y denotes a vector in which y(t) is enumerated.

For example, a sensor is a membrane-type surface stress sensor (MSS). The MSS has, as a receptor, a functional membrane to which a molecule adheres, and stress generated in a support member of the functional membrane is changed by adhesion and separation of the molecule to and from the functional membrane. The MSS outputs a detection value based on a change of the stress. Note that, a sensor is not limited to the MSS, and may be a sensor that outputs a detection value, based on a change in physical amount generated according to adhesion and separation of a molecule to and from the receptor and relating to viscoelasticity or a dynamic characteristic (mass, moment of inertia, or the like) of a member of the sensor, and various types of sensors such as cantilever type, membrane type, optical, piezoelectric, vibration-response sensors can be adopted.

Herein, when a sensor is an odor sensor, specific examples of use environment thereof include, for example, temperature, humidity, an air pressure, a type of contaminated gas, a type of purge gas, a sampling period of an odor component, a distance between a sensing target object and a sensor, an object existing around the sensor, and the like. Note that, a type of the contaminated gas is a type of gas supplied to the sensor together with a target odor component in an operation (sampling) of exposing the sensor to a target gas. Specifically, a type of the contaminated gas includes an inert gas such as nitrogen, air, and the like. A type of the purge gas is a gas supplied to the sensor in an operation (purge) of eliminating a measurement target gas from the sensor. Specifically, the purge gas includes an inert gas such as nitrogen, air, and the like. The sampling period of an odor component is a repetition period when an operation of exposing the sensor to a measurement target gas and an operation of eliminating the measurement target gas from the sensor are repeatedly performed. The distance between a target object and the sensor is a distance between the target object and the sensor in which the sensor is disposed around a specific target object and detection is performed. The object existing around the sensor is a type of target object in which the physical system 10 disposed around a specific target object and detection is performed.

Regarding Preprocessing

The present invention premises that a plurality of prediction models of the physical system 10 are prepared in advance in association with section information indicating a section matching a use environment of the physical system 10. Association between the prediction model and the section information is able to be generated by, for example, a method described below. However, the method described below is merely one example, and does not limit the present invention at all.

First, the information processing apparatus 20 generates an auto-regressive with exogenous input (ARX) model of the physical system 10 by use of time-series data (hereinafter, also referred to as "input-output time-series data") of input and output of the physical system 10. Herein, the information processing apparatus 20 generates an ARX model for each predetermined section by use of input-output time-series data for each section. Note that, a "section" is determined by a condition or an environment in which an input-output relation of a physical system to be a target becomes linear. As one example, a case where an input-output relation of a physical system to be a target becomes completely linear under any condition (environment) is considered. In this case, the number of sections of input-output time-series data is one. Further, in this case, the information processing apparatus 20 generates one ARX model by use of input-output time-series data for the one section. As another example, a case where an input-output relation of a physical system to be a target varies according to a specific condition (environment), and the physical system has a non-linear characteristic as a whole is considered. In this case, it can be said that the physical system has a local linearity when seen exclusively in a specific condition (environment). In other words, the number of sections of input-output time-series data becomes a plurality according to the number of specific conditions (environments) indicating a local linearity. Further, in this case, the information processing apparatus 20 generates an ARX model for each section by use of time-series data for each section indicating a local linearity (a section partially indicating a linearity) in the physical system. The present invention assumes that an input-output characteristic of the physical system 10 is basically non-linear, and there are a plurality of sections with regard to the input-output time-series data of the physical system 10.

Specifically, the information processing apparatus 20 first acquires a pair of the input time-series data 12 and the output time-series data 14 for each section, as input data for deriving a transfer function indicating a characteristic of a physical system to be a target. The input time-series data 12 and the output time-series data 14 for each section may be stored in, for example, a storage area (e.g., a storage device or the like of the information processing apparatus 20) accessible by the information processing apparatus 20, or may be acquired directly from the physical system 10.

The information processing apparatus 20 generates an ARX model for each section by use of the pair of the input time-series data 12 and the output time-series data 14 for each section. The information processing apparatus 20 can estimate a parameter of the ARX model (generate the ARX model) from the pair of the input time-series data 12 and the output time-series data 14 for each section by use of a known approach.

The information processing apparatus 20 generates a transfer function of the physical system for each section by use of the generated ARX model for each section. The information processing apparatus 20 can generate the transfer function for each section from the ARX model for each section by, for example, a procedure described below.

Herein, an ARX model of a physical system is represented by an equation (1) below. In the equation (1), y(t) is output (the output time-series data 14) of the physical system, u(t) is input (the input time-series data 12) to the physical system, $a_i$ is an auto-regressive coefficient, and $b_i$ is an exogenous input count. The information processing apparatus 20 can generate the ARX model indicated by the equation (1) below for each section by use of a combination of the input time-series data 12 and the output time-series data 14 classified into each section.

[Mathematical 1]

$$y(t) = \sum_{i=1}^{n} a_i y(t-i) + \sum_{i=1}^{m} b_i u(t-i) \tag{1}$$

By use of the ARX model generated for each section in this way, the information processing apparatus 20 generates a transfer function representing an input-output relation of a target physical system for each of the sections. The information processing apparatus 20 can obtain a transfer function in a z-area for each section by use of a result of performing a z-conversion of the ARX model for each section indicated by the equation (1) above. Specifically, the information processing apparatus 20 can obtain an equation (2) below by use of a result of performing the z-conversion of the equation (1) above. In the equation (2) below, Y(z)/U(z) is a ratio (i.e., a transfer function in a z-area) of the z-conversion of the output Y to the input U of the physical system.

[Mathematical 2]

$$\frac{Y(z)}{U(z)} = \frac{\sum_{i=1}^{m} b_i z^{-i}}{1 + \sum_{i=1}^{n} a_i z^{-i}} \tag{2}$$

Furthermore, the information processing apparatus 20 converts the transfer function in the z-area indicated by the equation (2) above into a transfer function based on Fourier transform by setting "$z=e^{i\omega\Delta t}$" in the equation (2) above. Herein, i is an imaginary number, ω is a frequency in Fourier transform, and Δt is a time interval of recording measurement data. As a result of the processing, the information processing apparatus 20 can obtain a model expressing, by a transfer function, a characteristic relating to an input-output of the target physical system 10.

Herein, an input-output relation of the physical system 10 may be influenced by a use environment (use condition) of the physical system. For example, in a case of a sensor or the like, a characteristic of a mechanism for converting input into output may change according to a measurement environment (measurement condition) of the sensor, and, as a result, a characteristic of the sensor may become non-linear as a whole. As a specific example, when a spring exists as one component of a sensor, a spring coefficient varies due to temperature, humidity, and the like, and a characteristic of the sensor can become non-linear. However, a section locally having a linearity can be found by finely classifying a measurement environment (measurement condition) such as temperature or humidity. From here, a section of input-output time-series data can be determined based on, for example, a measurement environment of the sensor.

With regard to a section based on a measurement environment (measurement condition) such as temperature, humidity, and air pressure, a boundary (threshold value) thereof can be automatically determined by utilizing, for example, heterogeneous mixture learning. The heterogeneous mixture learning is a technique for automatically learning, from data, "a prediction model (heterogeneous mixture prediction model) of separating input data into cases by a rule in a decision tree format, and predicting with a linear model combining explanatory variables differing from case to case". The heterogeneous mixture learning can simultaneously solve three "model selection problems": (1) a problem of determining the number of prediction equations; (2) a problem of determining the number and a type (a combination) of explanatory variables to be utilized for each prediction equation; and (3) a problem of determining a rule structure (=section) of dividing data. Note that, a detail of the heterogeneous mixture learning is disclosed in, for example, NPL 1 described above. A correspondence relation with section information is generated for each prediction model of the physical system 10 by the heterogeneous mixture learning, and stored in a storage area such as a storage device 1080. Another approach being capable of solving the "model selection problem" described above may be utilized instead of the heterogeneous mixture learning. A person who operates the information processing apparatus 20 may confirm each combination of the input time-series data 12 and the output time-series data 14, and determine a section for each prediction model.

Figure 4:
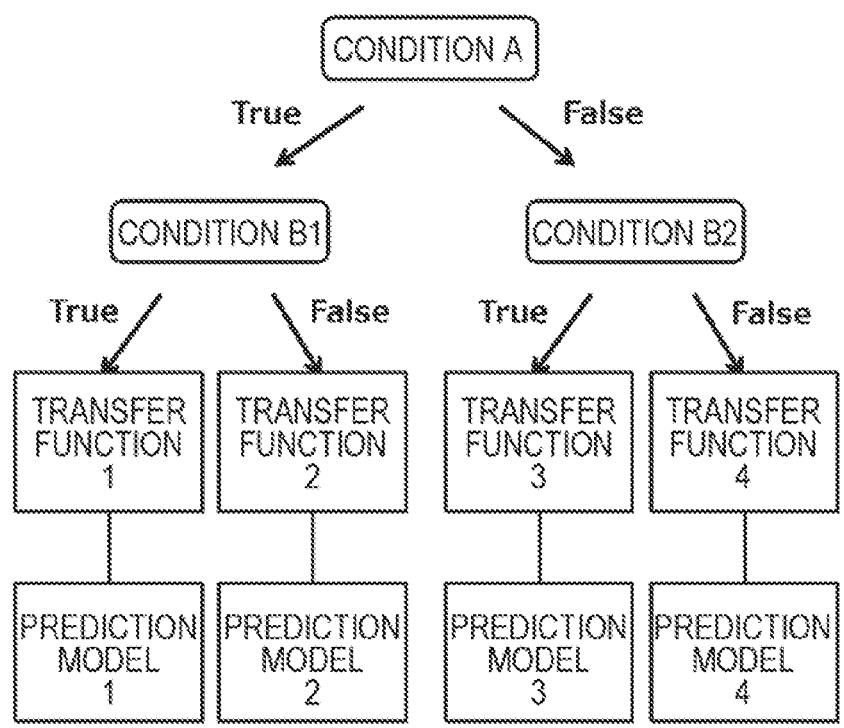
FIG. 4 is a diagram schematically illustrating one example of a correspondence relation between a prediction model and section information, generated by heterogeneous mixture learning.

FIG. 4 is a diagram schematically illustrating one example of a correspondence relation between a prediction model and section information, generated by heterogeneous mixture learning. FIG. 4 illustrates a modeled state of an overall input-output characteristic of the physical system 10. The model of the physical system 10 illustrated in FIG. 4 has a hierarchical structure including a plurality of nodes. A branch formula is located as a condition of branching at one or more intermediate nodes, and a transfer function is located at a node in a lowermost layer. In the present figure, a condition A, a condition B1, and a condition B2 are conditions of branching. Transfer functions 1 to 4 are transfer functions derived from input-output data of the physical system 10 of each section, based on a branch condition.

A combination of branch conditions for intermediate nodes through which to pass until arriving at each transfer function located in the lowermost layer falls under the section described above. A structure of the intermediate node is automatically generated as a result of, for example, heterogeneous mixture learning. The information processing apparatus 20 can determine, based on a section of an ARX model (a section of input-output time-series data used for generation of the ARX model), a position with which a transfer function derived from the ARX model is to be linked. As a specific example, it is assumed that the information processing apparatus 20 generates a certain transfer function from an ARX model generated based on input-output time-series data belonging to a section "condition A=FALSE, and condition B2=TRUE". In this case, the information processing apparatus 20 can link the transfer function to a position of the "transfer function 3" in FIG. 4, from the section "condition A=FALSE, and condition B2=TRUE".

A prediction model (prediction equation) is generated for each branch condition, from a feature value obtained by use of each transfer function. For example, a prediction model (prediction equation) is a linear sum of feature values, and represented by $z=WX+b$. Herein, X is a feature value vector based on output of the physical system 10 (sensor), W is a weight coefficient vector indicating a weight coefficient being relevant to each element (feature value) of the feature value vector X, and b is a constant, z being obtained indicates a prediction result. The prediction model (prediction equation) may be used for discrimination, or may be used for regressive prediction. For example, a prediction model (prediction equation) used for discrimination of presence or absence of a certain odor component can determine that a measurement target gas contains a detection target odor component when z is equal to or more than a predetermined reference, and determine that a measurement target gas does not contain the detection target odor component when z is less than the reference. An example of the regressive prediction includes prediction of product quality, based on an odor of a product such as a beverage, prediction of a state in a body by measurement of exhalation, or the like.

Herein, a prediction model (prediction equation) in which weighting of each feature value differs is generated for each branch condition by executing sparse learning such as least absolute shrinkage and selection operator (LASSO) by use of learning data for each branch condition. The prediction model (prediction equation) generated in this way is stored in a storage area (e.g., a storage device or the like of the information processing apparatus 20) accessible by the information processing apparatus 20 in association with information (i.e., section information) indicating a branch condition related to the prediction model (prediction equation).

Note that, an apparatus other than the information processing apparatus 20 may execute each step described herein instead of the information processing apparatus 20, and the information processing apparatus 20 may utilize a result generated by the other apparatus.

Hardware Configuration Example

Each functional component of the information processing apparatus 20 may be achieved by hardware (example: a hard-wired electronic circuit, or the like) that achieves each functional component, or may be achieved by a combination of hardware and software (example: a combination of an electronic circuit and a program controlling the electronic circuit, or the like). A case where each functional component of the information processing apparatus 20 is achieved by a combination of hardware and software is further described below.

Figure 5:
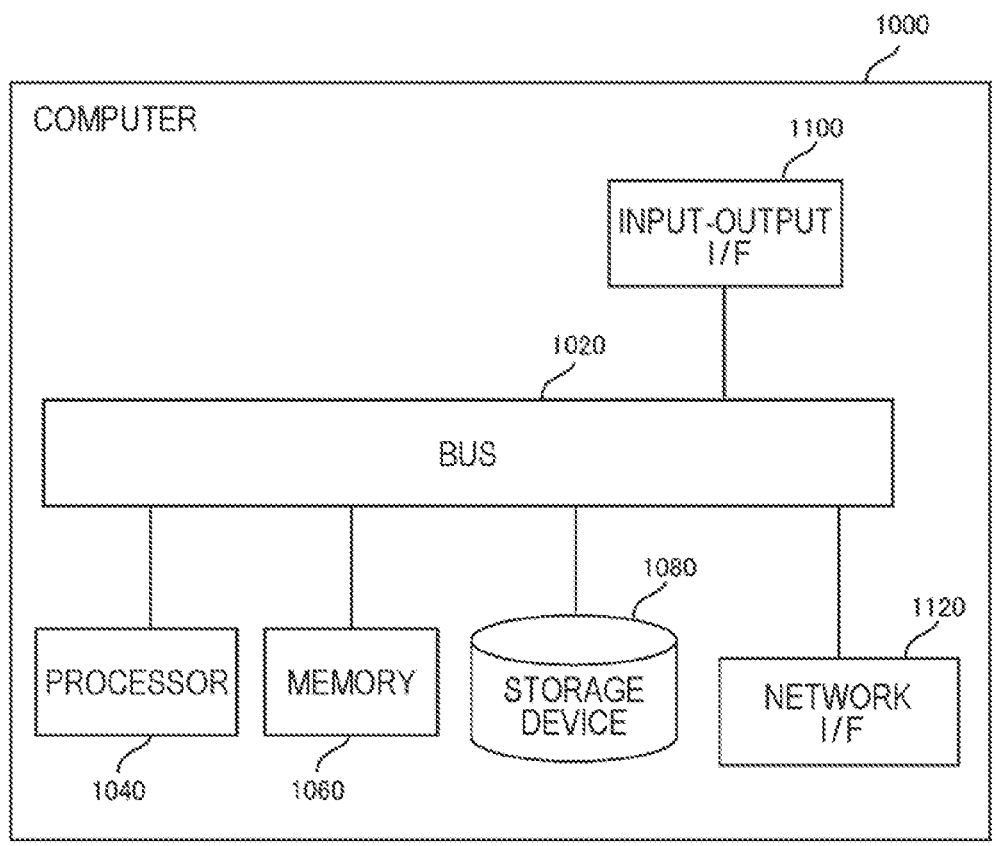
FIG. 5 is a diagram illustrating a computer for achieving the information processing apparatus.

FIG. 5 is a diagram illustrating a computer 1000 for achieving the information processing apparatus 20. The computer 1000 is any computer. For example, the computer 1000 is a stationary computer such as a personal computer (PC) or a server machine. Additionally, for example, the computer 1000 is a portable computer such as a smartphone or a tablet terminal. The computer 1000 may be a dedicated computer designed to achieve the information processing apparatus 20, or may be a general-purpose computer.

The computer 1000 includes a bus 1020, a processor 1040, a memory 1060, a storage device 1080, an input-output interface 1100, and a network interface 1120. The bus 1020 is a data transmission path through which the processor 1040, the memory 1060, the storage device 1080, the input-output interface 1100, and the network interface 1120 are transmit/receive data to/from each other. However, a method of mutually connecting the processor 1040 and the like is not limited to bus connection.

The processor 1040 includes various types of processors such as a central processing unit (CPU), a graphics processing unit (GPU), and a field-programmable gate array (FPGA). The memory 1060 is a main storage apparatus achieved by use of a random access memory (RAM) or the like. The storage device 1080 is an auxiliary storage apparatus achieved by use of a hard disk, a solid state drive (SSD), a memory card, a read only memory (ROM), or the like.

The input-output interface 1100 is an interface for connecting the computer 1000 and an input-output device. The input-output interface 1100 is connected, for example, an input apparatus such as a keyboard and an output apparatus such as a display apparatus. In addition thereto, the input-output interface 1100 is connected to, for example, the physical system 10 being a sensor or the like. However, it is not always necessary for the physical system 10 such as a sensor to be directly connected to the computer 1000. For example, the physical system 10 such as a sensor may cause a storage apparatus shared with the computer 1000 to store the input time-series data 12 and the output time-series data 14.

The network interface 1120 is an interface for connecting the computer 1000 to a communication network. The communication network is, for example, a local area network (LAN) or a wide area network (WAN). A method of connecting the network interface 1120 to a communication network may be wireless connection or may be wired connection.

The storage device 1080 stores a program module that achieves each of function-configuring units (the use environment information acquisition unit 210, the model selection unit 220, the prediction unit 230, and the like) of the information processing apparatus 20. The processor 1040 reads each of the program modules onto the memory 1060, executes the read program module, and thereby achieves a function relevant to each of the program modules.

Flow of Processing

A flow of processing executed by the information processing apparatus 20 is described below by use of a figure.

Figure 6:
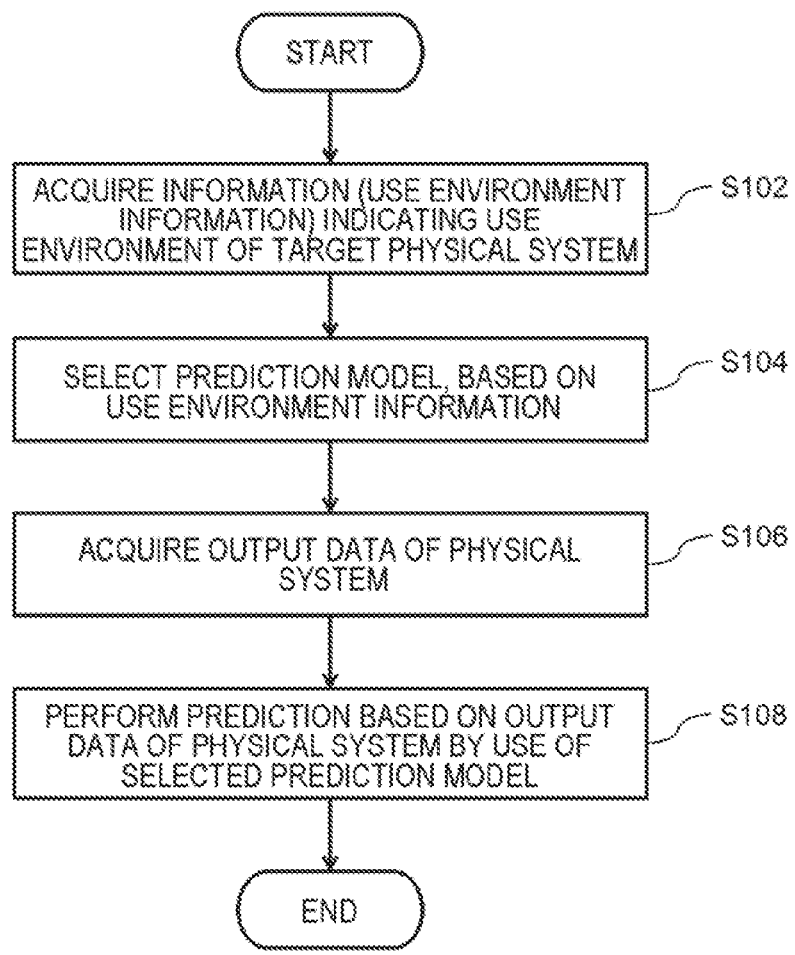
FIG. 6 is a flowchart illustrating a flow of processing executed by the information processing apparatus.

FIG. 6 is a flowchart illustrating a flow of processing executed by the information processing apparatus 20.

First, the use environment information acquisition unit 210 acquires use environment information of the physical system 10 to be a target (S102). The model selection unit 220 specifies, by use of information (example: FIG. 7) of a plurality of prediction models prepared in advance, a section matching a use environment indicated by the use environment information (S104). FIG. 7 is a diagram illustrating one example of information associating a prediction model with section information. The information illustrated in FIG. 7 is stored in, for example, the storage device 1080 or the like. In the information illustrated in FIG. 7, four sections are defined by two threshold values $T_1$ and $T_2$ relating to temperature and a threshold value $H_1$ relating to humidity, and a deferring prediction model is set for each section. As one example, when the use environment information acquired in the processing at S102 indicates "temperature T>threshold value $T_1$, and temperature T≥threshold value $T_2$", the model selection unit 220 can select a "prediction model 2" by use of the information illustrated in FIG. 7.

The prediction unit 230 acquires output data of the physical system 10 to be a target (S106). The prediction unit 230 may acquire, for example, real-time output data from the physical system 10 connected via the input-output interface 1100 or the network interface 1120. The prediction unit 230 may acquire output data of the physical system 10 via a storage apparatus (not illustrated) that stores the output data of the physical system 10. The prediction unit 230 performs prediction based on the acquired output data or feature data obtained from the output data, by use of the prediction model selected in the processing at S104, and outputs a result of the prediction to a display for a user or the like (S108).

Advantageous Effect

As above, in the present example embodiment, a prediction model for performing prediction, based on output data of the physical system 10, is first selected according to a use environment of the physical system 10. In other words, an appropriate prediction model is selected according to a use environment of the physical system 10. Prediction based on output data of the physical system 10 is performed by use of the selected prediction model. Thus, an effect of reducing a possibility that a wrong prediction result is obtained from the output data of the physical system 10, and improving accuracy of the prediction can be expected.

While the example embodiments of the present invention have been described with reference to the drawings, the example embodiments are only exemplification of the present invention, and various configurations other than the above-described example embodiments can also be employed.

Further, a plurality of steps (processing) are described in order in the flowchart used in the description given above, but an execution order of the steps is not limited to the described order. According to the example embodiment described above, an order of the illustrated steps can be modified within an extent that there is no harm in context.

What is claimed is:

1. A system comprising:
    an odor sensor having a receptor to which a contaminant molecule contained in a gas is adherable, the odor sensor exposing the receptor to the gas, detecting detection values in response to adhesion of the contaminant molecule to the receptor and separation of the contaminant molecule from the receptor, and purging the gas from the odor sensor;
a processor; and
a memory storing instructions executable by the processor to:
acquire use environment information indicating a use environment of the odor sensor, the use environment including at least one of temperature, humidity, air pressure, a type of the contaminant molecule detectable in the gas, a type of the gas to which the receptor is exposed, a sampling time period in which the receptor is exposed to the contaminant molecule, and a distance from the odor sensor to a target object as to which the contaminant molecule is to be detected;
select, from a plurality of prediction models for the odor sensor respectively associated with different use environments, the prediction model associated with the use environment of the odor sensor; and
perform prediction as to presence or absence of the contaminant molecule based on the detection values detected by the odor sensor, using the selected prediction model.

2. The information processing apparatus according to claim 1, wherein the instructions are executable by the processor to further
generate correspondence relations between the prediction models and the different use environments are respectively by heterogeneous mixture learning.

3. An information processing method executed by a computer of a system that also includes an odor sensor, the odor sensor having a receptor to which a contaminant molecule contained in a gas is adherable, the odor sensor exposing the receptor to the gas, detecting detection values in response to adhesion of the contaminant molecule to the receptor and separation of the contaminant molecule from the receptor, and purging the gas from the odor sensor, the method comprising:
acquiring use environment information indicating a use environment of the odor sensor, the use environment including at least one of temperature, humidity, air pressure, a type of the contaminant molecule detectable in the gas, a type of the gas to which the receptor is exposed, a sampling time period in which the receptor is exposed to the contaminant molecule, and a distance from the odor sensor to a target object as to which the contaminant molecule is to be detected;
selecting, from a plurality of prediction models for the odor sensor respectively associated with different use environments, the prediction model associated with the use environment of the odor sensor; and
performing prediction as to presence or absence of the contaminant molecule based on the detection values detected by the odor sensor, using the selected prediction model.

4. The information processing method according to claim 3, further comprising
generating correspondence relations between the prediction models and the different use environments are respectively by heterogeneous mixture learning.

5. A non-transitory computer readable medium storing a program causing a computer of a system to execute an information processing method, the sensor also including an odor sensor, the odor sensor having a receptor to which a contaminant molecule contained in a gas is adherable, the odor sensor exposing the receptor to the gas, detecting detection values in response to adhesion of the contaminant molecule to the receptor and separation of the contaminant molecule from the receptor, and purging the gas from the odor sensor, the method comprising:
acquiring use environment information indicating a use environment of the odor sensor, the use environment including at least one of temperature, humidity, air pressure, a type of the contaminant molecule detectable in the gas, a type of the gas to which the receptor is exposed, a sampling time period in which the receptor is exposed to the contaminant molecule, and a distance from the odor sensor to a target object as to which the contaminant molecule is to be detected;
selecting, from a plurality of prediction models for the odor sensor respectively associated with different use environments, the prediction model associated with the use environment of the odor sensor; and
performing prediction as to presence or absence of the contaminant molecule based on the detection values detected by the odor sensor, using the selected prediction model.

* * * * *